United States Patent [19]

Kamen

[11] Patent Number: 4,563,177
[45] Date of Patent: Jan. 7, 1986

[54] CATHETER STABILIZATION PAD

[76] Inventor: Dean L. Kamen, 44 Gage Rd., Bedford, N.H. 03102

[21] Appl. No.: 564,519

[22] Filed: Dec. 22, 1983

[51] Int. Cl.⁴ ............................................. A61M 5/00
[52] U.S. Cl. ............................. 604/177; 128/DIG. 26
[58] Field of Search ..................... 128/133, DIG. 26; 604/164–165, 174, 177, 179, 180

[56] References Cited

U.S. PATENT DOCUMENTS

| | | | |
|---|---|---|---|
| 3,834,380 | 9/1974 | Boyd | 128/DIG. 26 |
| 4,129,128 | 12/1978 | McFarlane | 604/174 X |
| 4,250,880 | 2/1981 | Gordon | 128/DIG. 26 |
| 4,366,817 | 1/1983 | Thomas | 604/174 |
| 4,392,856 | 7/1983 | Lichtenstein | 604/177 |
| 4,445,893 | 5/1984 | Bodicky | 604/177 X |
| 4,484,913 | 11/1984 | Swauger | 604/179 |

*Primary Examiner*—Dalton L. Truluck
*Attorney, Agent, or Firm*—Bromberg, Sunstein & McGregor

[57] ABSTRACT

A unitary sheet device for removably securing a catheter to the skin of a patient includes a pair of flaps for being affixed to the skin and a central portion performed in a contour conforming to the catheter hub. When affixed, the central portion and the patient's skin together form a receptacle for securely holding the catheter against movement. The central portion may be a tapered conical sheet and the flaps may have adhesive for ease of attachment. A detent is provided, which may include a hole through the central portion of the sheet for engaging a protrusion from the catheter hub. Flexing of the sheet disengages the detent. A non-adhesive tab on one flap aids in removing the device.

3 Claims, 6 Drawing Figures

U.S. Patent  Jan. 7, 1986  Sheet 1 of 2  4,563,177
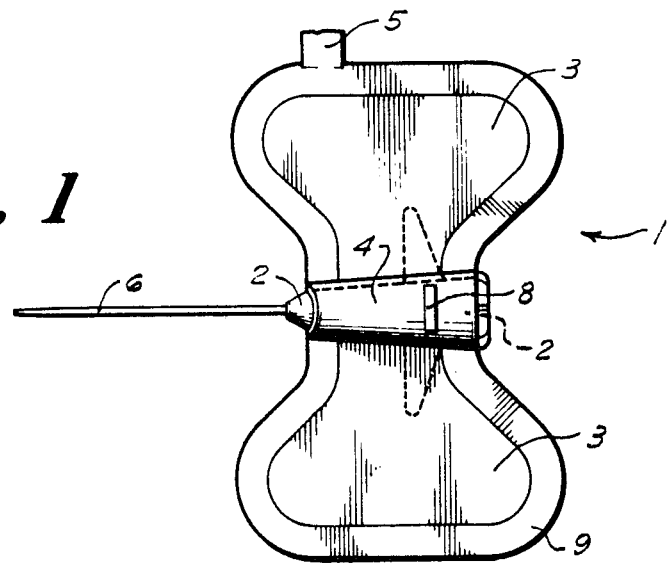
FIG. 1
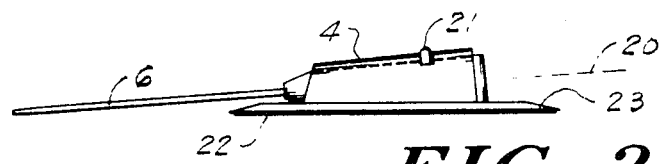
FIG. 2
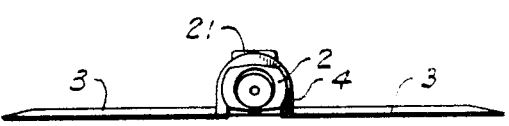
FIG. 3
FIG. 4
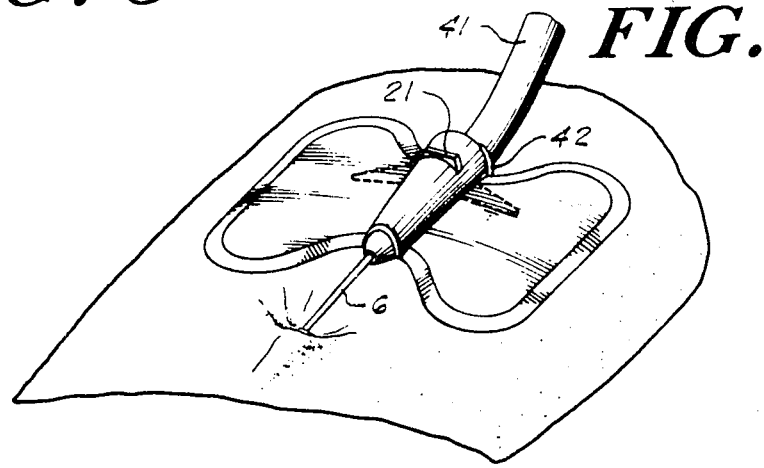

CATHETER STABILIZATION PAD

DESCRIPTION

1. Technical Field

The present invention relates to methods and devices for holding down an infusion catheter to prevent unwanted motion of such catheter when attached to the body of a patient, and more particularly to such a device which allows detachment of the catheter from the body of the patient without requiring prior removal of the device.

2. Background Art

It is common hospital practice to administer medicines or other fluids to a patient via an infusion tube attached to an intravenous needle or catheter attached to a patient's limb. The needle or catheter must be manually inserted to a precise location, which may be intravenous, intramuscular or subcutaneous, and thereafter this location must be maintained as appropriate for the particular infusion fluid, despite the possible twisting and turning of the patient or the motion of the appended infusion tubing. In practice, the catheter tube or needle extends from a more substantial catheter hub body to which the infusion tubing is attached; the body has a pair of laterally extending flanges which are generally taped to the patient to prevent extraneous motion of the assembly. Because even minor motions of the body could lead to movement of, or pressure on, a needle assembly, it is common to employ a hollow plastic catheter tube as the element which penetrates the skin to deliver the medication. This tube is initially installed by inserting a conventional needle therethrough and puncturing the skin of the patient for insertion, thereafter withdrawing the needle and leaving the infusion tube as a flexible attachment to the patient. This allows a slight amount of bending of the tube itself, or motion of the catheter hub body, without breaking or kinking of the flow path, or local trauma caused by wobbling of the needle due to lateral pressure being transmitted. However the taping of a catheter body to the skin of the patient is cumbersome, and the catheter may not be removed from the patient thereafter without removing the tape. It can be traumatic for a patient to have adhesive tape painfully pulled from his skin prior to removal of the catheter.

Several devices have been patented for holding such an assembly in a stable position. Thus the device of U.S. Pat. No. 4,129,128 shows a hold-down device with a pair of wings and a central housing, wherein the wings may be taped securely to the body of a patient and the central housing has end walls adapted to receive the laterally extending "ears" of a catheter hub. U.S. Pat. No. 3,900,026 shows a rigid rectangular box-like structure, with a flexible neck which engages the catheter hub, the whole rectangular housing forming a protective shield for the needle and being secured to the body of a patient by an adhesive flange extending around the perimeter. Neither of these devices appears to permit removal of the catheter from the patient's body without prior removal of the hold-down device. There is thus a need for a simple catheter stabilization device capable of securely holding a catheter against unwanted movement yet allowing release of the catheter and removal thereof from the patient without requiring prior removal of the stabilization device.

BRIEF DESCRIPTION OF THE INVENTION

The present invention is a flexible catheter stabilization device formed of sheet material having a pair of laterally protruding flaps on either side of the axis defined by the catheter, and connected by a central portion having a contour for receiving the body of the catheter hub. In a preferred embodiment, the contour is tapered and a hole or detent in the central portion engages a corresponding element of the catheter hub to prevent motion of the catheter assembly along the axis defined by the catheter tube. In a further preferred embodiment the tapered central portion is of conical shape, and pinching the flaps together releases the hub so it may be withdrawn without removing the stabilization pad from the body of the patient. An adhesive band around the perimeter of the flaps on the lower side thereof permits easy application of the pad to the patient, in an adhesive tape-like fashion, after the catheter has been inserted. A non-adhesive tab on one flap aids in gripping the pad for removal after use. A beveled edge portion provides greater flexibility and compliance of the adhesive perimeter of the flaps, for more secure attachment to contoured surfaces. These and other features of the invention will be more readily understood by reference to the drawings.

BRIEF DESCRIPTION OF THE DRAWINGS

FIG. 1 shows a top view of the catheter stabilization pad according to the present invention;

FIG. 2 shows a side view thereof;

FIG. 3 shows a front view from the catheter end of the present invention;

FIG. 4 shows a perspective view of the pad adhered to the limb of a patient;

DESCRIPTION OF SPECIFIC EMBODIMENTS

Figure 5:
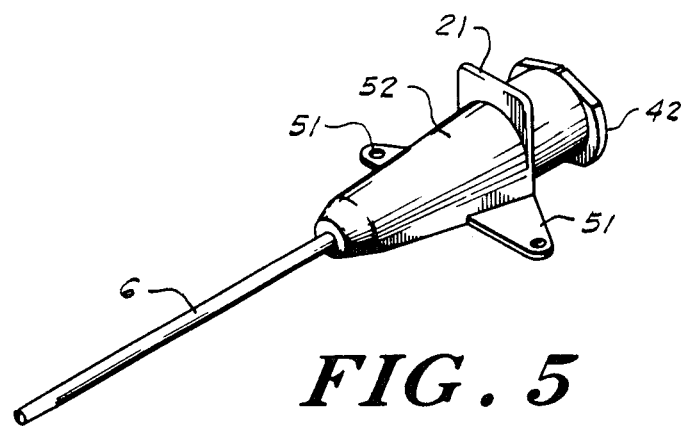
FIG. 5 shows a catheter and hub with detent adapted to the pad of FIG. 1.

Referring to FIG. 1 there is shown a basic embodiment of the stabilization pad 1 of the present invention, having flaps 3 disposed on either side of a central portion 4. The unit may be made of a molded polyethylene, or vacu-formed from sheet stock of any appropriate flexible plastic. As shown, central portion 4 is adapted to receive the hub 4 of a catheter (shown in phantom) having a catheter tube 6 extending therefrom. Also shown in FIG. 1 is an aperture 8 in the central portion 4 for receiving a corresponding detent or protrusion from the catheter hub and holding the hub secure against axial motion. The perimeter portion 9 of the stabilization pad is preferably treated with an adhesive on the underside thereof so that the pad may be applied like a self-adhesive bandage without requiring external taping or straps to hold it securely on the body of the patient. A tab 5, not having adhesive thereon, but protruding from one wing, serves as a grip to aid in removal of the stabilization pad. As may be seen, the two flaps 3 extend on either side of the catheter body and are approximately symmetrically disposed in relation to the axis defined by the catheter tube 6.

Turning now to FIG. 2, it may be seen that the axis 20 defined by the tube 6 is a central axis of the catheter hub 2. It is conventional for a catheter hub to have a central bore, into which a needle is inserted to stiffen and stabilize the flexible plastic tube 6 to permit insertion thereof through the skin of a patient. Also conventional catheter hubs generally have the external profile of a slightly tapered cone. Such a profile allows the hub body to rest in a position approximately tangential to the skin of the patient when the needle has been inserted, at an angle, to an appropriate depth. In the present device, advantage is taken of this conical profile by providing a contoured tapered sheet surface as the central portion 4, which conformably fits against the profile of the catheter hub. As shown, the central portion 4 narrows as it gets closer to the catheter tube end of the hub. Also shown in FIG. 2 is a nub 21 projecting upward from the body of the catheter hub and through the aperture 8 of FIG. 1. The stabilization pad itself is formed of a flexible but relatively thick sheet. The top surface thereof, around the edges 9 of FIG. 1, is beveled as shown at 23 in FIG. 2, thus effectively thinning the edge portion and permitting a greater pliability in that area. The underside of beveled surface 23 bears an adhesive layer 22 for attaching to the body of a patient. The adhesive need not extend entirely around the perimeter, and indeed, where it is desired to remove the catheter without first removing the pad, it is advisable to omit the adhesive near the central regions of the pad so that the "ears" appearing on a normal catheter may easily slide under the perimeter portion thereof for removal.

Turning now to FIG. 3, there is shown an end view of the stabilization pad according to the present device in which the flaps 3 at each side attach to the center portion 4 which conformally wraps around the catheter hub 2. The protruding nub 21 may be seen projecting up through the sheet of the center portion 4.

FIG. 4 shows a catheter stabilization pad according to the present invention in use, with infusion tubing or inlet connection tubing 41 leading into the hub and catheter tube 6 extending from the front of the hub through the skin of the patient. It will be appreciated that the taper of the central portion permits the catheter to slide into a secure position and subsequently be retained there as the protruding nub 21 reaches the retaining aperture 8 thereby locking the hub into position. As the catheter is inserted there becomes progressively less looseness for maneuvering the hub and upon full insertion the hub is firmly held on all sides against motion. The laterally projecting hub "ears" shown in phantom prevent any twisting of the hub which could cause kinking of the inlet tube or of the catheter tube 6. The conformable contour of the central portion prevents any lateral motion whatsoever; and the detent system comprising the aperture 8 and nub 21 prevents any axial motion. In this manner, the catheter stabilization pad provides an unprecedented degree of stability of the catheter itself. Nonetheless, in the event it is desired to remove the catheter from the body of the patient, as for instance upon discharge, or simply to employ a different vein for the infusion, the catheter hub may be released from the stabilization pad by simply pinching together the skin of the patient in the area of the two wings, thus causing the central portion to rise up releasing the nub 21 and allowing the withdrawal of the hub from the central portion along axis 20. The stabilization pad itself is not situated over the actual site of needle insertion, and therefore may be left in place without worry of infection or other consequences until such time as it may be removed without trauma to the patient. In this manner the association of physical pain with the insertion or removal of needles or catheters is entirely avoided, thus eliminating one of the common negative experiences of modern hospital practice.

Turning now to FIG. 5, there is shown a detailed view of the catheter employed with the present stabilization pad. As noted above, the pad itself is generally adapted or adaptable to common catheters currently used, requiring in addition only a detent or projection, like nub 21, to provide the axial stability of the invention. Such a catheter is shown having flexible catheter tube 6 extending from a tapered hub 52. Hub 52 has a pair of laterally extending wings 51 of relatively small dimension which define a plane at the bottom thereof which rests against the skin of the patent and serves to prevent rotation of the hub 52 in use. Extending from the top of hub 52 is a nub 21 in the form of a straight tab. It is clear that nub 21 may be of virtually any shape so long as it mates with the corresponding aperture 8 of FIG. 1 so as to prevent motion along the catheter axis 20. Similarly wings 51 may be quite small. Unlike the "ears" of a conventional catheter, they need not be taped to the body but serve only the residual purpose of providing a flat orientation against the skin. Similarly, tapered hub 52 may be of virtually any cross-sectional shape, such as a long thin pyramidal shape and need not be conical. The purpose of the taper, in addition to the conventional function of defining a guide for the needle used in inserting tube 6 through the skin, is largely to allow progressively more secure insertion of the body within the stabilizing central portion 4 of the stabilization pad. At the rearmost edge of the catheter hub is flange 42, which extends a slight distance radially outward so as to butt against the edge of the stabilization pad and provide a well-defined stop to limit insertion. While the use of nub 21 and aperture 8 suffices to axially secure the device, the flange 42 adds further restraint against wobble.

Figure 6:
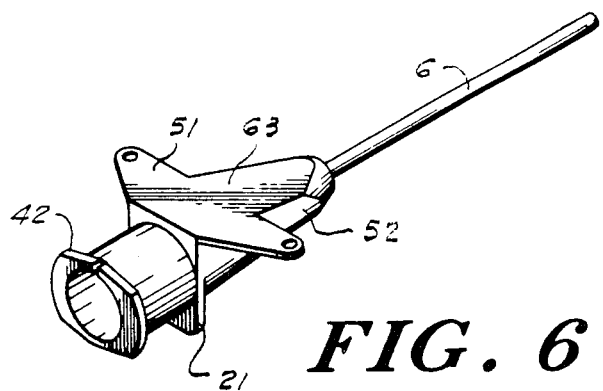
FIG. 6 shows a bottom view of the catheter and hub of FIG. 5.

Turning now to FIG. 6, there is shown a bottom view of the catheter of FIG. 5. As may be seen, the lower portion 63 of body 52 is flat and forms a common plane with wings 51 so as to rest on the skin of the patient without twisting. Lower edge of flange 42, which would only bear against the skin of the patient, is removed.

It will be appreciated that the precise shape of wings 51 is of little importance, as long as they project somewhat laterally to prevent twisting of the device, and the invention may be practiced altogether without such wings, if lower surface 63 of the catheter body is of sufficient size to assure that the hub 4 does not rotate. However, in the event wings 51 are used, it will be appreciated that a portion of the stabilization pad 1 located adjacent to the central portion should not have any adhesive in a location which would interfere with withdrawal of the catheter from the stabilization pad.

In one embodiment of the invention, wings 51 measure ½ inch (13 mm), tip to tip, and the catheter hub is approximately 3/16 (5 mm) of an inch in diameter at its large end. The stabilization pad itself measures 2¼ inches (56 mm), side to side, with a maximum front to back dimension of 1½ inches (38 mm) and has a beveled peripheral region 1/16 of an inch (1½ mm) wide. The catheter hub is ¾ inches (19 mm), tip to tip, and both the rear flange 42 and the nub 21 extend approximately 1/32 (0.75 mm) of an inch and have a thickness of approximately 0.040 inches (1 mm). The stabilization pad provides a high degree of stability and comfort, isolating the catheter tube from the incidental motions of the infusion tube 41.

It will be appreciated that the present invention requires no rigid housing and presents an elastic structure which can removably engage a catheter hub so as to permit sanitary and simple maintenance of the hub in position yet allow convenient removal as needed, without any trauma upon removal. It will be appreciated that the invention may readily be practice with a wide variety of flexible plastic or rubber-like material; it may be practiced with adhesive or non-adhesive flaps, in which case the flaps may be attached with adhesive tape as in a conventional catheter hub. The taper of the central portion may conveniently be of any shape adapted to fit the catheter hub so long as the pad and hub together have a detent means for preventing axial motion after insertion. Similarly the detent may include any means of mating protruding elements, preferably of an aperture and nub variety, which may be released by squeezing together the wings of the pad in such a way as to cause the central portion to flex away from the catheter hub. Accordingly, the invention is limited only by the following claims.

What is claimed is:

1. A stabilization pad for securely holding to the body of a patient a catheter, having a hub with a stop member projecting radially therefrom and a catheter tube extending therefrom, the pad comprising:
   a flexible sheet having:
   (i) a central contoured portion defining an inside surface substantially conformal to a portion of the external profile of the catheter hub, such central portion having an aperture extending entirely therethrough for receiving the stop member and securing the hub, and
   (ii) a pair of laterally extending flap portions disposed on either side of the central portion, each of such flap portions having on the same side of the sheet as the inside surface a layer of adhesive for adhering the pad to the skin of a patient, wherein a sufficiently large region of each flap portion proximate to the central contoured portion is devoid of adhesive, so that the catheter may be removed from the patient by pinching together the flap portions to separate the central portion from the hub to permit removal of the catheter without detaching the pad from the skin.

2. A stabilization pad according to claim 1, wherein a flap portion includes a protruding tab without a layer of adhesive thereon for use as a grip in removing the pad from the patient.

3. A stabilization pad according to claim 1, wherein the hub has a pair of wings projecting outwardly from opposite sides thereof, such wings defining a plane perpendicular to the stop member and on the opposite side of the hub therefrom, and wherein the portion of each flap devoid of adhesive is just sufficient in area to avoid contact of the wings with the adhesive layer when the pad is used and when the catheter is removed therefrom.

* * * * *